United States Patent [19]
Wales

[11] Patent Number: 5,800,449
[45] Date of Patent: Sep. 1, 1998

[54] KNIFE SHIELD FOR SURGICAL INSTRUMENTS

[75] Inventor: Kenneth S. Wales, Mason, Ohio

[73] Assignee: Ethicon Endo-Surgery, Inc., Cincinnati, Ohio

[21] Appl. No.: 816,017

[22] Filed: Mar. 11, 1997

[51] Int. Cl.⁶ .................................. A61B 17/32
[52] U.S. Cl. .................. 606/172; 606/170; 606/205; 606/206; 606/207; 606/46; 606/48
[58] Field of Search .................. 606/170, 172, 606/205, 206, 207, 37, 41, 45, 46, 48, 49, 50, 51, 52, 167

[56] References Cited

U.S. PATENT DOCUMENTS

| | | | |
|---|---|---|---|
| 2,068,721 | 1/1937 | Wappler et al. | 128/303.15 |
| 4,655,216 | 4/1987 | Tischer | 128/303.1 |
| 5,174,300 | 12/1992 | Bales et al. | 128/751 |
| 5,258,006 | 11/1993 | Rydell et al. | 606/205 |
| 5,342,359 | 8/1994 | Rydell | 606/51 |
| 5,403,342 | 4/1995 | Tovey et al. | 606/205 |
| 5,445,638 | 8/1995 | Rydell et al. | 606/51 |
| 5,458,598 | 10/1995 | Feinberg et al. | 606/52 |
| 5,462,546 | 10/1995 | Rydell | 606/51 |
| 5,527,319 | 6/1996 | Green et al. | 606/170 |
| 5,573,534 | 11/1996 | Stone | 606/48 |
| 5,573,535 | 11/1996 | Viklund | 606/51 |

Primary Examiner—Michael Powell Buiz
Assistant Examiner—Daphna Shai
Attorney, Agent, or Firm—Bernard Shay

[57] ABSTRACT

A surgical instrument according to the present invention includes a handle, an elongated closure tube, an end effector, a pair of wireform elements which may be, for example, wireform conductors, extending through the elongated tube from the handle to the end effector and a knife blade at the end effector and a tissue stop adapted to shield the knife blade when the knife blade is in its proximal most position. In a surgical instrument according to the present invention, the wireform elements are positioned within wireform guide channels formed in the tissue stop. In a surgical instrument according to the present invention, the closure tube includes a tissue stop including a distal end and a proximal end. The tissue stop further includes a body, a neck a knife housing and knife channel, the knife channel being adapted to support the shank of the knife as it moves within the knife channel.

9 Claims, 7 Drawing Sheets

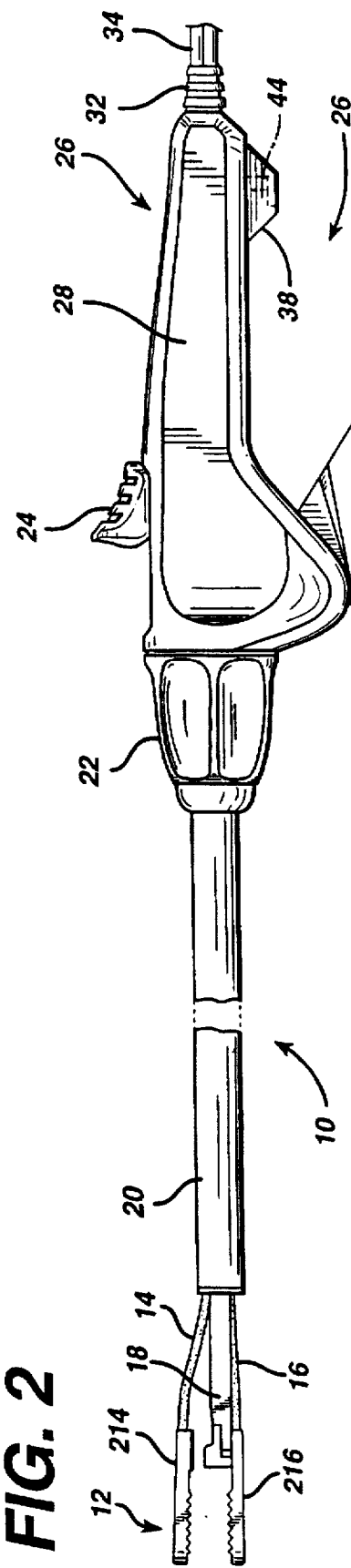
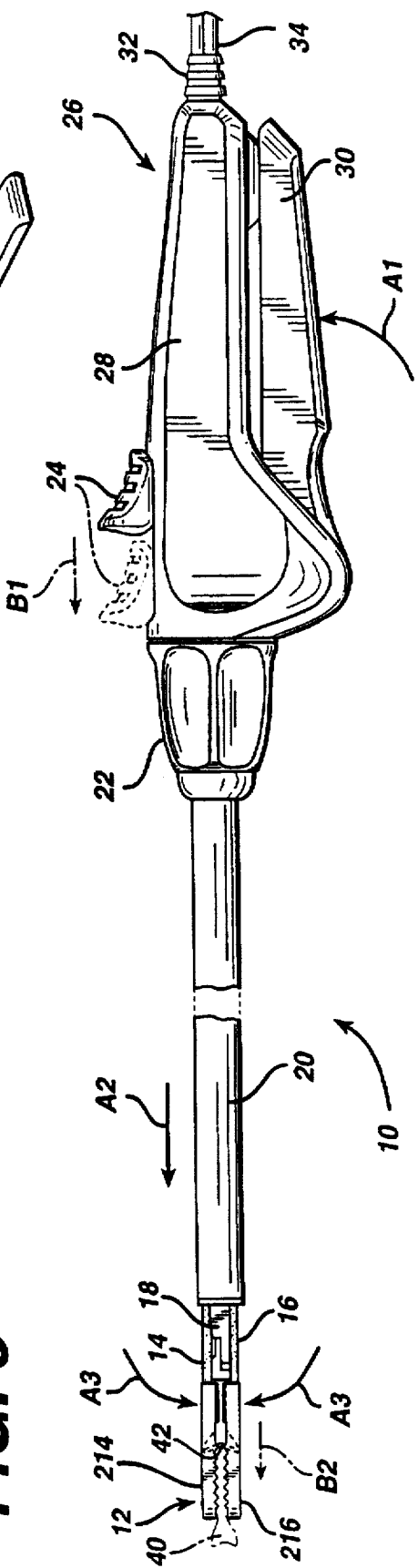

KNIFE SHIELD FOR SURGICAL INSTRUMENTS

This application is related to the following patent applications: application Ser. No. 08/537,065; application Ser. No. 08/536,726; application Ser. No. 08/751,898; application Ser. No. 08/555,741; application Ser. No. 08/761,411; application Ser. No. 08/762,218; and application, Ser. No. 08/816,020.

FIELD OF THE INVENTION

The present invention relates, in general, to a tissue stop for use with a surgical instrument and, more particularly, to an improved tissue stop including a knife shield for use with an electrosurgical instrument.

BACKGROUND OF THE INVENTION

Electrosurgical instruments are used by surgeons to apply electrosurgical energy to tissue. Electrosurgical devices are used for effecting improved hemostasis by heating tissue and blood vessels to cause coagulation or cauterization. Monopolar electrosurgical devices utilize one active electrode associated with the cutting or cauterizing instrument and a remote return or ground electrode which is usually attached externally to the patient. Thus, in surgery utilizing monopolar instruments, electrical current passes from the active electrode, through the patient to the return electrode. In bipolar electrosurgical instruments, both electrodes are included on the instrument and, generally, both electrodes are active. Thus a typical bipolar instrument includes two or more electrodes which are charged to different electrical potentials. In bipolar electrosurgical instruments, the tissue is treated by passing electrical current through tissue positioned between the electrodes.

Electrical energy is used in medical instruments for a number of purposes including hemostasis, i.e. to stop or slow bleeding in tissue. Application of electrical current in conjunction with pressure applied by the end effector of a surgical instrument results in a significant reduction in bleeding. Thus, electrical current may be used to cauterize tissue prior to cutting the tissue, reducing or eliminating bleeding around the cut. The electrical current which passes through the tissue acts to heat the tissue. As the tissue is heated, it changes in color and texture. The experienced surgeon may, by looking for changes in the color or texture of the tissue around the end effector, determine when to turn off the current to the end effector. Once the tissue has been treated and the current turned off, the tissue grasped by the end effector may be cut by, for example, advancing a knife blade through the tissue in the end effector.

Bipolar forceps, being one type of bipolar electrosurgical instrument, have been used in various procedures for coagulating tissue. Generally bipolar forceps include two opposing jaws each connected to an output electrode of an electrical generator such that, when the generator is turned on, the opposing jaws are charged to different electrical potentials. Organic tissue being electrically conductive, the charged electrodes apply electrical current through the grasped tissue. Once the tissue has been treated to limit blood flow, a knife or other cutting instrument may be used to cut the tissue. In most such devices, the knife is positioned to travel through a knife channel in the instrument wherein the knife channel positions and supports the knife as it moves. In such devices, tissue stops act to prevent tissue from being positioned past the proximal end of the end effector.

In other electrosurgical instruments such as certain types of bipolar forceps, the end effector includes a knife channel capable of supporting the knife as it moves through the jaws of the end effector. In such devices it would be desirable to protect tissue engaged by the jaws of the forceps until the surgeon desires to cut the engaged tissue. It would also be desirable to limit the travel of the knife to the length of the end effector in order limit the amount of motion the surgeon has to apply to cut engaged tissue. In bipolar forceps wherein the jaws of the end effector are supported by wireform conductors it may be difficult to align the jaws of the end effector as the end effector is closed since the jaws may have a tendency to shift as the closure tube passes over the wireform conductors. It would, therefore, be advantageous to design a tissue stop including a knife shield such that when the knife is in its proximal most position, the knife blade is positioned in the knife shield within the tissue stop and the distal end of the tissue stop is between the jaws. It would also be advantageous to design a tissue stop which includes a support channel adapted to provide support to the knife as it travels through the end effector. Finally, it would be advantageous to design a tissue stop as set forth above wherein the tissue stop included guide channels for the wireform conductors, the guide channels being adapted to guide and support the wireform conductors as the closure tube moves in a proximal to distal direction.

SUMMARY OF THE INVENTION

A surgical instrument according to the present invention includes a handle, an elongated closure tube, an end effector, a pair of wireform elements which may be, for example, wireform conductors, extending through the elongated tube from the handle to the end effector and a knife blade at the end effector and a tissue stop adapted to shield the knife blade when the knife blade is in its proximal most position. The wireform conductors are connected to and support the jaws of the end effector. The knife blade is connected to the handle through a push bar which passes through the elongated tube. In a surgical instrument according to the present invention, the push bar is positioned between the wireform elements and is axially moveable with respect to the wireform elements. In addition, in a surgical instrument according to the present invention, the wireform elements are positioned within wireform guide channels formed in the tissue stop.

In a surgical instrument according to the present invention, the closure tube includes a tissue stop including a distal end and a proximal end. The distal end of the tissue stop includes a knife blade slot. The tissue stop further includes a knife channel connecting the distal end to the proximal end, the knife channel being adapted to support the shank of the knife as it moves within the knife channel. In addition, first and second wireform guide channels are formed on the exterior surface of the tissue stop. In a further embodiment of the present invention, the wireform guide channels include rib elements which are adapted to mate with slots in said wireform elements to position the wireform elements and hold the tissue stop in place as the closure tube is moved from its proximal to its distal position.

In a further embodiment of the present invention, the tissue stop includes a body at its proximal end, a knife housing at its distal end and a neck portion connecting said body and said knife housing. In this embodiment of the present invention, the knife housing is positioned between the jaws of the end effector and includes an elongated slot adapted to receive a knife blade. The neck portion of the tissue stop is positioned at the intersection of the end effector jaws and the wireforms while the body is positioned proximal of the jaws of the end effector. In a further embodiment of the present invention, one of the jaws is affixed to the tissue stop.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is a side elevational view of an electrosurgical instrument shown with the jaws of the end effector in a first, unclamped position.

FIG. 3 is a side elevational view of an electrosurgical instrument shown with the jaws of the end effector in a second, clamped position.

DETAILED DESCRIPTION OF THE INVENTION

Figure 1:
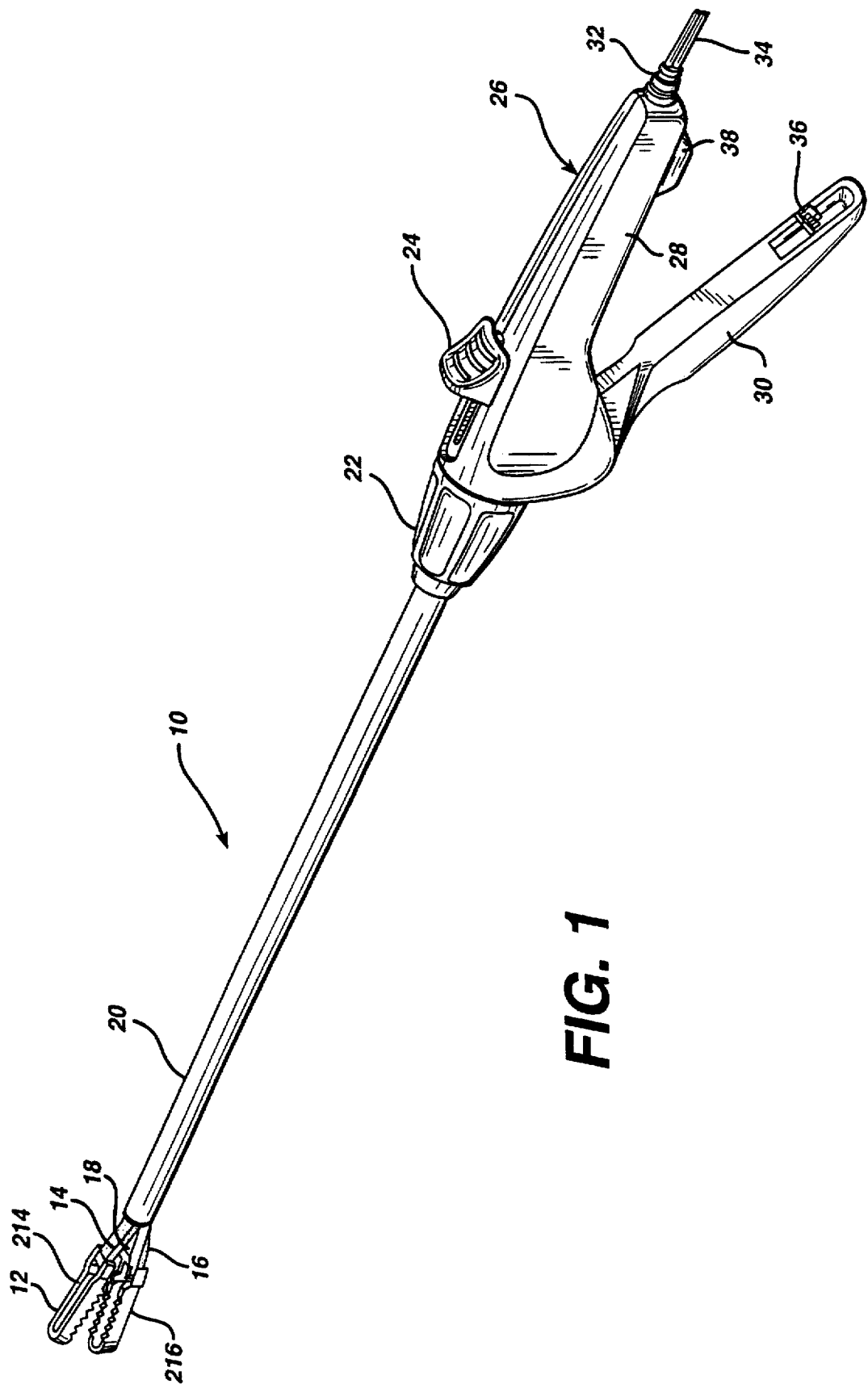
FIG. 1 is a perspective view of an electrosurgical instrument.

FIG. 1 is a perspective view of a surgical instrument according to the present invention. The surgical instrument of FIG. 1 may be referred to herein as a bipolar forceps. In bipolar forceps 10, illustrated in FIG. 1, jaws 214 and 216 of end effector 12 are supported by upper wireform 14 and lower wireform 16. Wire forms 14 and 16 may also act as electrical conductors, supplying bipolar electrical energy to end effector 12. Tissue stop 18 is positioned within tube 20. Tube 20 may be, for the present example, an elongated hollow closure tube extending from handle 26 toward end effector 12. Rotation knob 22 is attached to closure tube 20 to cause rotation of closure tube 20 and end effector 12 with respect to handle 26. Handle 26 includes knife button 24, grip 28 and trigger 30. Electrical cord 34 is connected to handle 26 through strain relief 32. Trigger latch 36 is positioned on trigger 30. Handle latch shield 38 is positioned on grip 28.

As illustrated in FIG. 2, end effector 12 of bipolar forceps 10 has a first open position when trigger 30 is open. As illustrated in FIG. 3, end effector 12 of bipolar forceps 10 has a second closed position when trigger 30 is in the closed position. Movement of trigger 30 in direction A1 moves closure tube 20 in direction A2 to force wireforms 14 and 16 together, forcing the jaws of end effector 12 in direction A3. In the closed position, as illustrated in FIG. 3, end effector 12 is adapted to grasp tissue 40. Tissue 40 is positioned within jaws 214 and 216 at the proximal end of end effector 12. The distal end of tissue stop 18 prevents tissue 40 from moving past the grasping portion of jaws 214 and 216. In addition, the distal end of tissue stop 18 positions tissue 40 adjacent to knife blade 94 to facilitate cutting. Movement of knife button 24 in direction B1 moves knife 42 out of tissue stop 18 in direction B2. Movement of knife 42 in direction B2 cuts tissue positioned in end effector 12.

Figure 4:
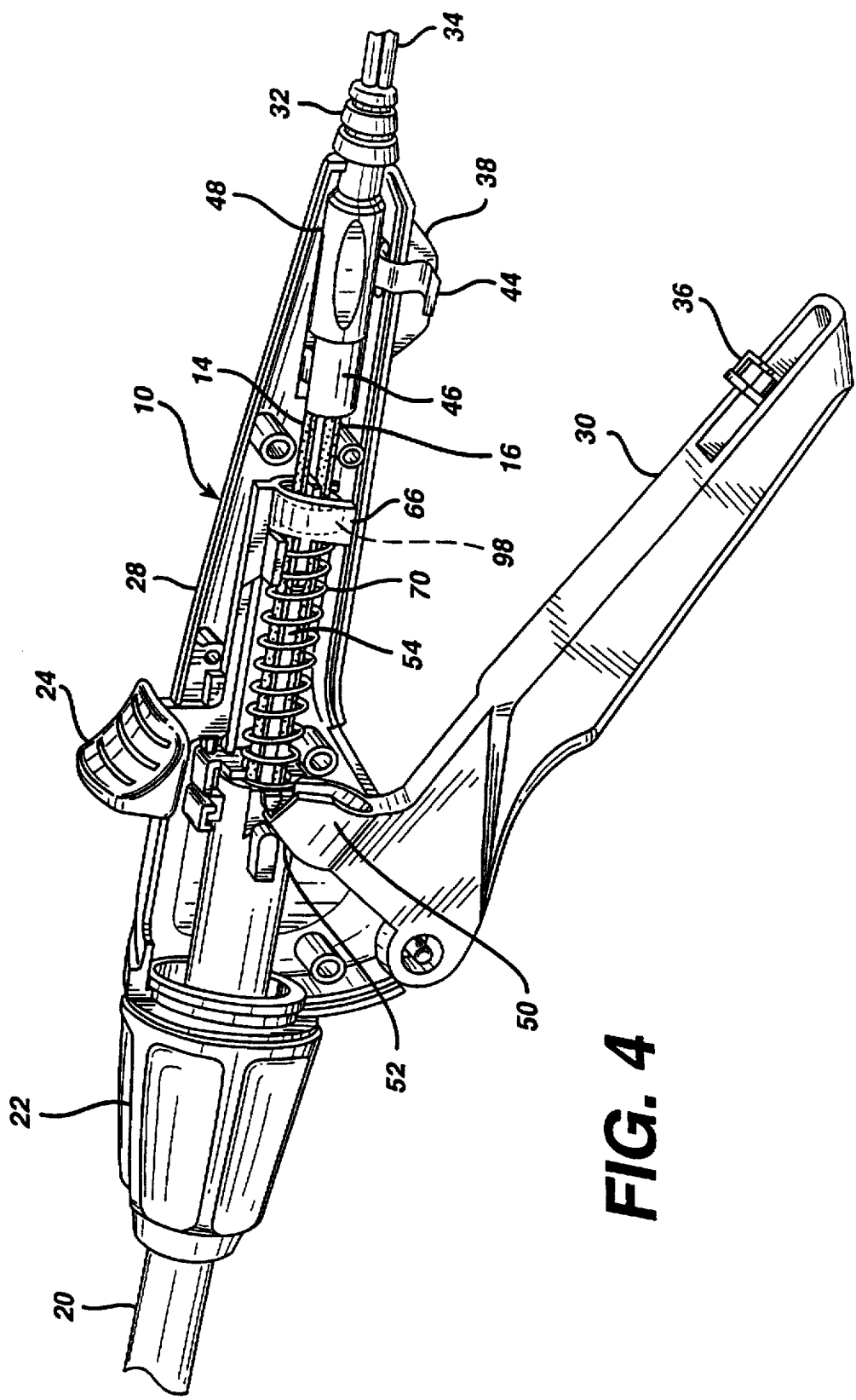
FIG. 4 is a perspective view of an electrosurgical instrument of the present invention with the left side of the handle removed.

FIG. 4 is a perspective view of bipolar forceps 10 with the left side of grip 28 removed. In FIG. 4, handle latch 44 is illustrated. Wire form anchor 46, which is adapted to receive the proximal end of upper wireform 14 and lower wireform 16, is attached to interior strain relief 48 which in turn is a part of strain relief 32. Trigger yoke 50 on trigger 30 may include trigger yoke cam face 52.

Figure 5:
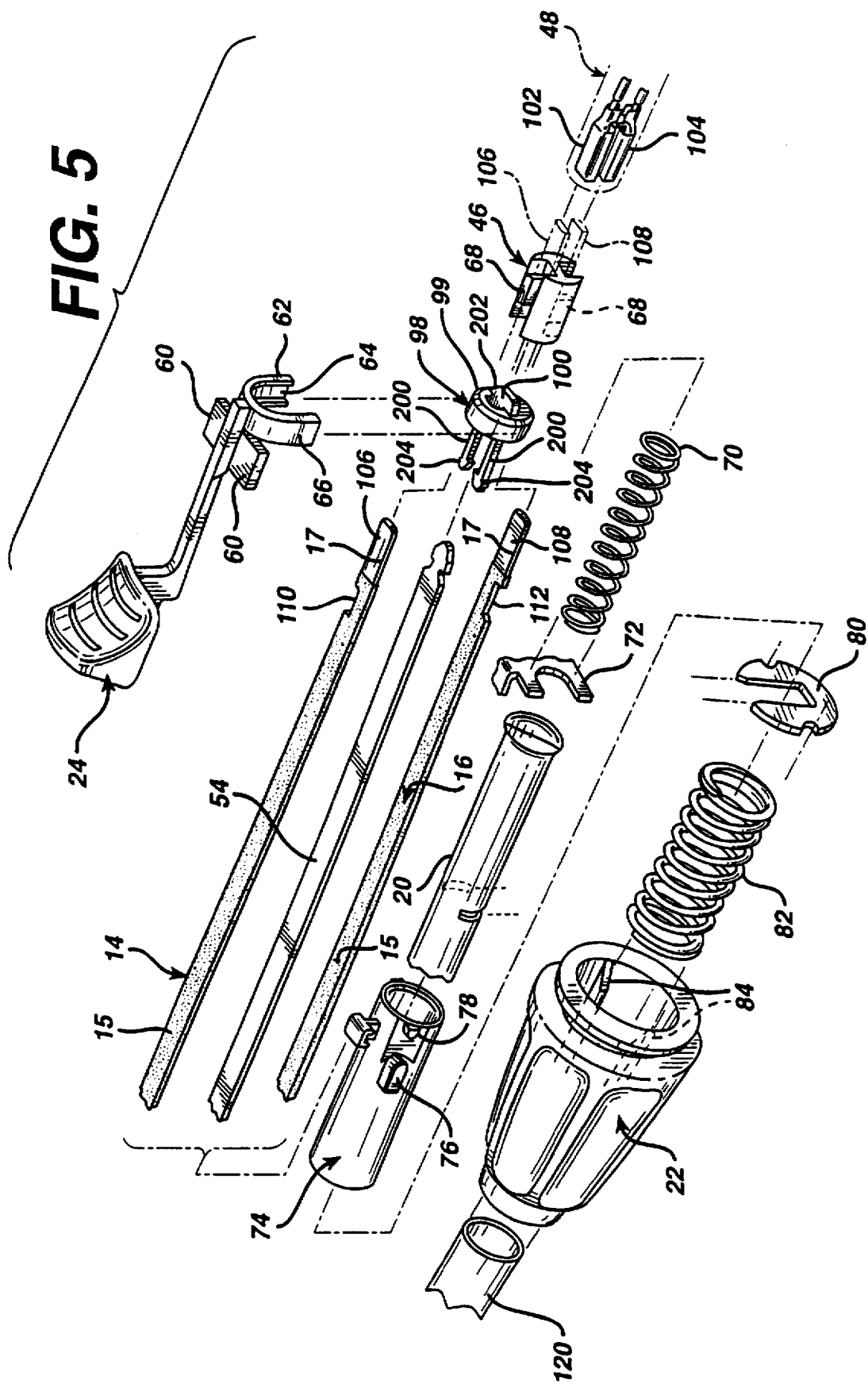
FIG. 5 is an exploded view of a portion of the internal mechanism of the handle illustrated in FIG. 4.

FIG. 5 is an exploded view of a portion of the internal mechanism of the handle illustrated in FIG. 4. In FIG. 5, the proximal end of push bar 54 is adapted to fit with connector 100 in hub 98. In the embodiment of the invention illustrated in FIG. 5, connector 100 and hub 98 cooperate to form coupler 99. Ribs 60 on knife button 24 are adapted to slide within the handle and guide knife button 24 as it moves axially along the handle 26. Yoke 62 of knife button 24 includes hub slot 64 which is adapted to receive knife hub 98. Rib 68 of wireform anchor 46 is adapted to fit within slots 110 and 112 of upper wireform 14 and lower wireform 16, respectively. Wireforms 14 and 16 each include insulation layer 15 and an electrical conductor 17. Knife return spring 70 works against knife spring retainer 72 to provide a counter force which counters the movement of button 24 in direction B1. Closure tube collar 74 is adapted to fit over the proximal end of closure tube 20 and includes drive rib 76 and retract rib 78, which interact with trigger yoke 50 as illustrated in FIG. 4. Closure tube washer 80 is adapted to fit within slots in closure tube 20 to hold closure tube collar 74 in place. Closure tube washer 80 also acts to retain trigger return spring 82. Closure tube washer 80 is guided axially by washer ribs 84 and rotation knob 22. Electrical connectors 102 and 104 are positioned within interior strain relief 48 and connected to upper wireform proximal connector 106 and lower wireform proximal connector 108 respectively to form an electrical connection between wireforms 14 and 16 and chord 34. Slot 110 in upper wireform 14 and slot 112 in lower wireform 16 are adapted to mate with ribs 68 and 69, respectively, in wireform anchor 46.

In FIG. 5, coupler 99 comprises hub 98 and a connector 100 disposed within hub 98. Connector 100 includes a pair of connector legs 200 and a bridge 202 connecting connected legs 200. Connector legs 200 include hooks 204 which are designed to grasp the push bar 54 such that axial movement of coupler 99 moves push bar 54 along the axis of elongated tube 20. In addition, rotational movement of coupler 99 results in rotational movement of push bar 54. Wireforms 14 and 16 pass through hub 98 of coupler 99 on either side of connector 100, thus allowing coupler 99 and push bar 54 to move axially without moving wireforms 14 and 16 axially. Rotational movement of coupler 99, on the other hand, results in rotational movement of wireforms 14 and 16 in conjunction with push bar 54. Thus, where wireforms 14 and 16 are connected to jaws 214 and 216 of end effector 12 and push bar 54 is connected to a working tool such as knife 42, the working tool may be moved axially independent of wireforms 14 and 16 of end effector 12 while the working tool moves rotationally in conjunction with wireforms 14 and 16 and with end effector 12.

Figure 6:
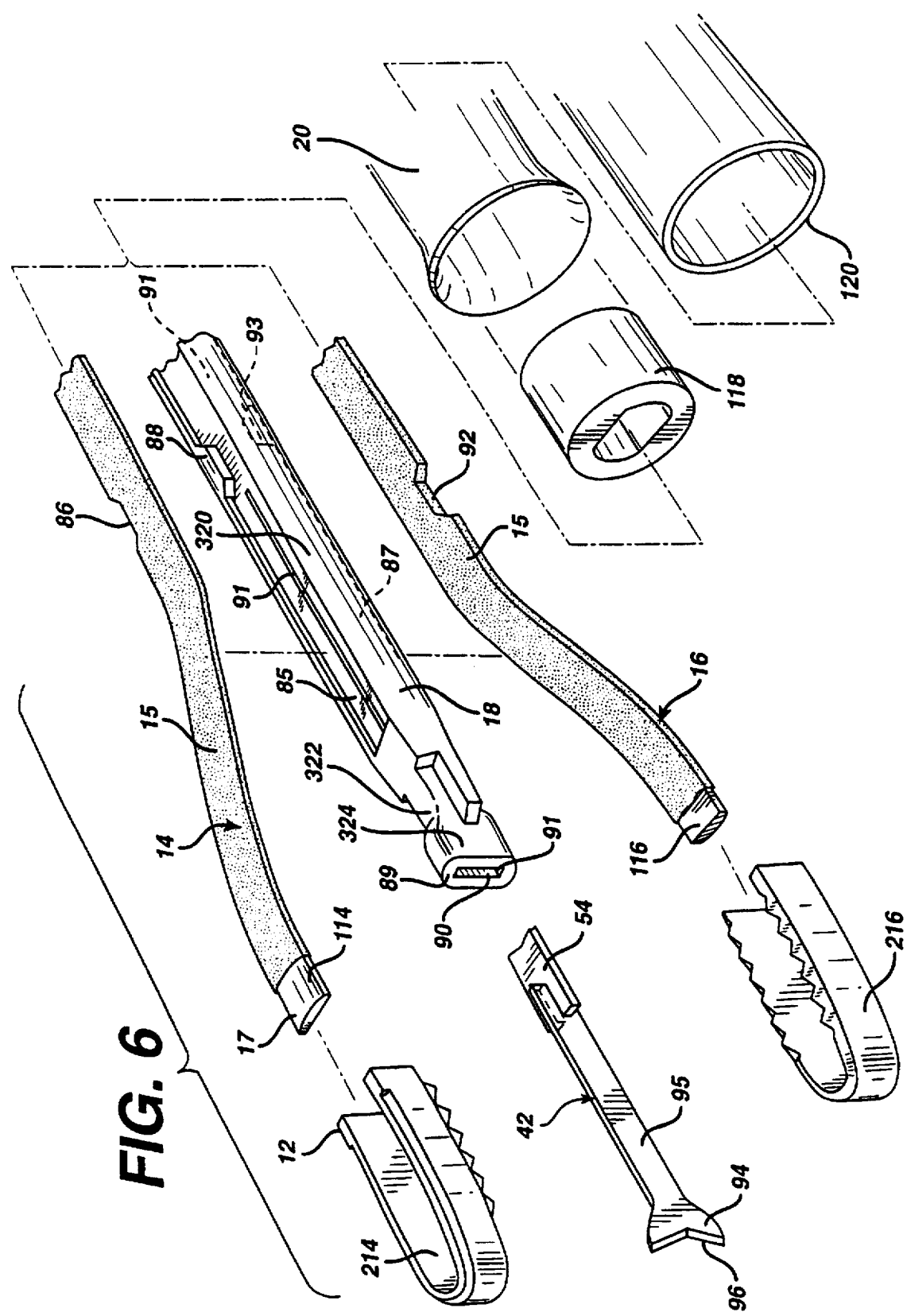
FIG. 6 is an exploded perspective view of a portion of the internal mechanism at the distal end of one embodiment of an electrosurgical instrument including a tissue stop according to the present invention.

FIG. 6 is an exploded perspective view of the internal mechanisms of bipolar forceps 10 at the distal end of closure tube 20. In FIG. 6, upper wireform distal connector 114 may be soldered or welded to upper end effector jaw 214 to form a mechanical and electrical connection between jaw 12 and wireform 14. Similarly, lower wireform distal connector 116 may be soldered or welded to lower end effector jaw 216. Upper wireform 14 and lower wireform 16 are biased away from tissue stop 18 at their distal end. Therefore, jaws 214 and 216 of end effector 12 are biased in the open position when closure tube 20 is retracted. Wireforms 14 and 16 may be biased away from tissue stop 18 by, for example, spring action resulting from forming wireforms 14 and 16 with an outward bend near their distal end, as illustrated in FIG. 6. End effector 12 may be closed by forcing wireforms 14 and 16 together, thus forcing jaws 214 and 216 together. As illustrated in FIG. 4, knife 42, which is connected to knife button 24 by push bar 54 and coupler 99, includes knife blade 94 and knife edge 96. Upper wireform 14, and lower wireform 16 pass through gas seal 118 which is positioned in the distal end of closure tube 20. Tissue stop 18 is positioned distal to gas seal 118. Closure tube 20 may be surrounded by an electrical insulator 120 such as shrink wrap tubing. Slot 86 in upper wireform 14 is adapted to mate with rib 88 in tissue stop 18. Similarly, slot 92 in lower wireform 16 is adapted to mate with rib 93 in tissue stop 18. Slot 90 in tissue stop 18 is adapted to receive knife blade 94 when knife button 24 is in its proximal position (i.e. when it is retracted). Knife slot 90 also acts to protect knife edge 96 of knife blade 94. Thus, tissue stop 18 may alternately be referred to as a knife guard.

In the embodiment of the invention illustrated in FIG. 6, tissue stop 18 is positioned within closure tube 20 and held in place by closure tube 20 and ribs 88 and 93 which fit into slots 86 and 92 of upper wireform 14 and lower wireform 16 respectively. Ribs 88 and 93 are located within wireform guide channels 85 and 87, respectively. Knife shank 95 and push bar 54 pass through tissue stop knife channel 91 which extends from the proximal end of tissue stop 18 to slot 90 in end surface 89 at the distal end of tissue stop 18. Knife channel 91 is adapted to support knife shank 95 and push bar 54, thus providing support to knife blade 94 as it moves from its proximal position to its distal most position. At least a portion of knife channel 91 conforms to the shape of knife shank 95 to provide support to knife shank 95. Knife blade slot 90 is adapted to receive knife blade 94, shielding knife edge 96 from tissue positioned in end effector 12 when knife 42 is in its proximal most postion. Distal end surface 89 of tissue stop 18 prevents tissue grasped by end effector 12 from contacting knife edge 96 and, in addition, positions the tissue within jaws 214 and 216 by preventing the tissue from moving past the proximal end of end effector 12.

Figure 7:
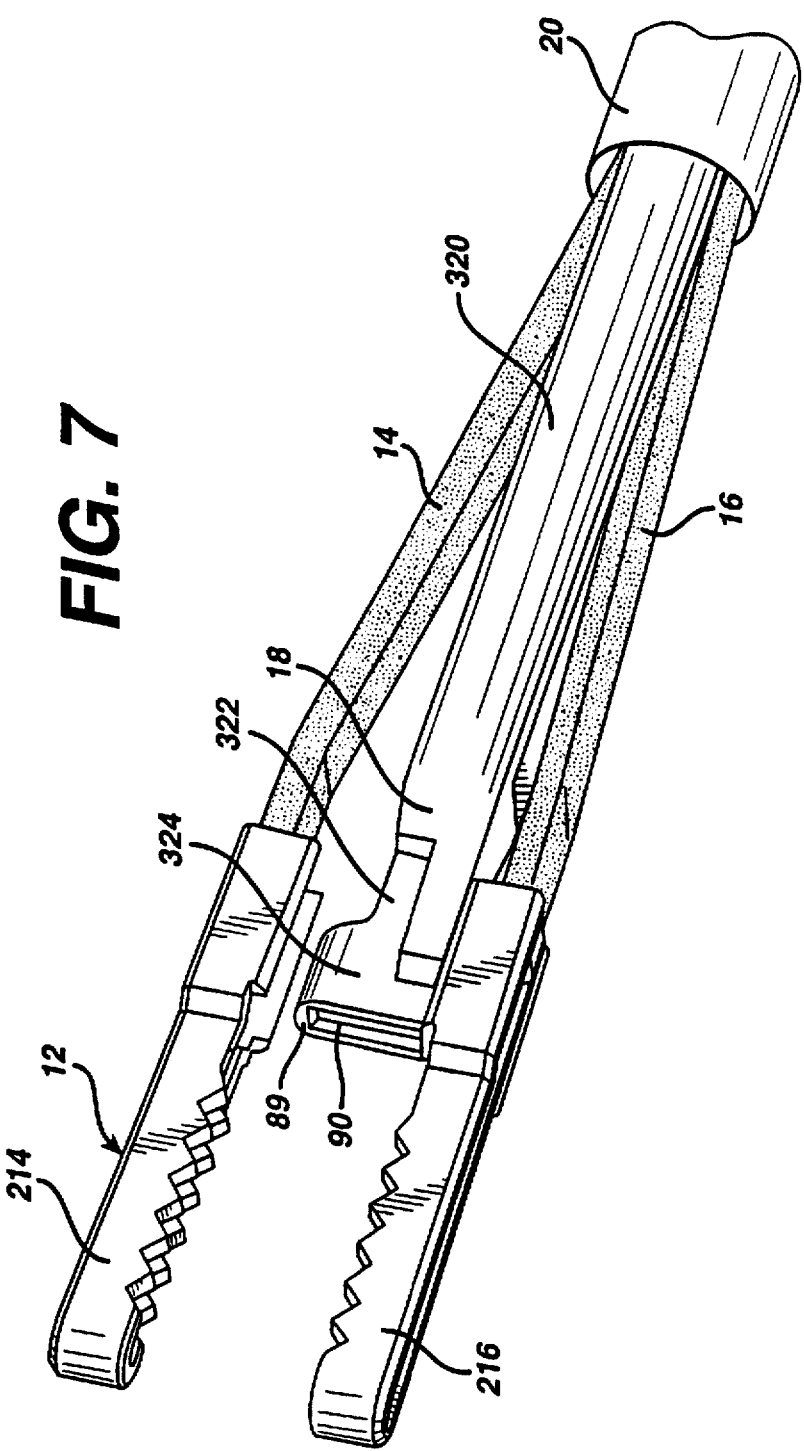
FIG. 7 is a perspective view of an end effector according to one embodiment of the present invention.
Figure 8:
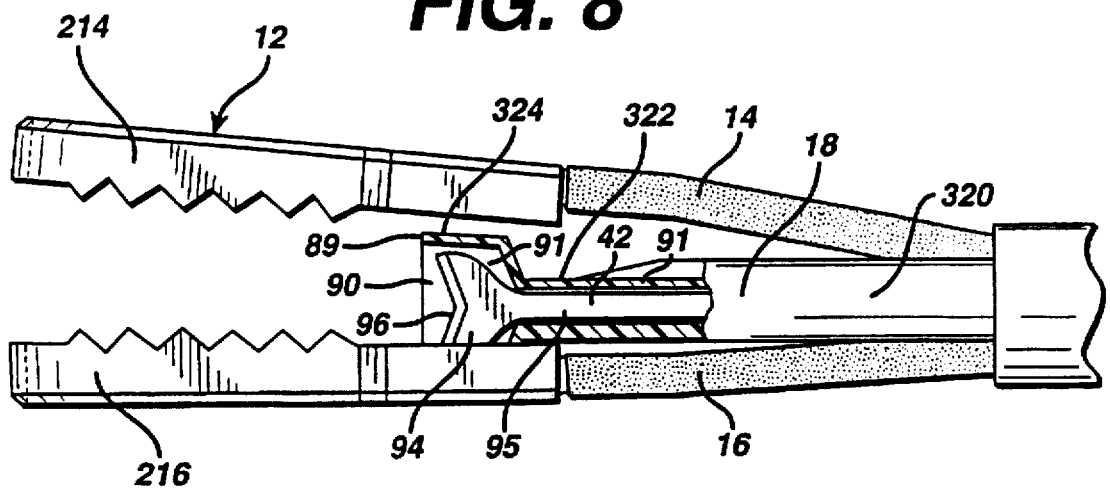
FIG. 8 is a side view of the end effector according to one embodiment of the present invention.
Figure 9:
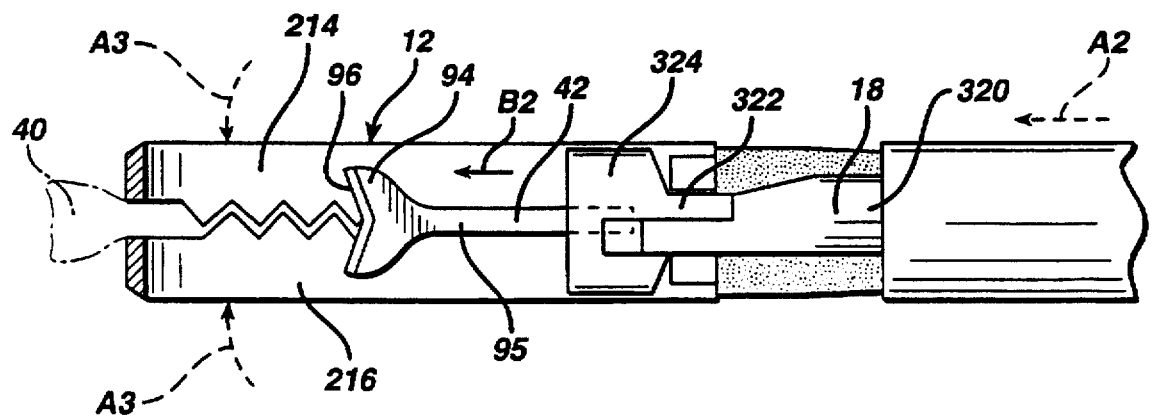
FIG. 9 is a side view of an end effector according to one embodiment of the present invention.

As illustrated in FIGS. 7–9, in an alternate embodiment of the present invention, one of jaw 214 or jaw 216 may be fixed in place by, for example, fixing one of upper wireform 14 or lower wireform 16 to tissue stop 18. Alternatively, one of jaw 214 or jaw 216 may be fixed in place by, for example, biasing one of upper wireform 14 or lower wireform 16 against tissue stop 18. Wireforms 14 or 16 may be biased toward tissue stop 18 by, for example, spring action resulting from forming wireforms 14 or 16 with an inward bend near their distal end.

Referring now to FIGS. 7–9, tissue stop 18 includes a body 320, a neck 322 and a blade housing 324. Body 320 includes knife channel 91 and upper slot 86 and lower slot 92 which are adapted to receive, hold and guide wireforms 14 and 16. Neck 322 of tissue stop 18 is adapted to connect blade housing 324 to body 320. Neck 322 is positioned at the intersection of wireforms 14 and 16 with jaws 214 and 216.

Because neck 322 is positioned at the intersection of jaws 214 and 216 with wire forms 14 and 16 it is smaller than either body 320 or blade housing 324. Blade housing 324 is positioned within jaws 214 and 216 and distal to the distal ends of wireforms 14 and 16. Blade housing 324, being adapted to hold blade 94 and to include end surface 89 is larger than neck 322 and is elongated in shape. Blade housing 324 has an elongated shape to guide jaw 214 to mate with jaw 216 as end effector 52 is closed. The shape of tissue stop 18 is particularly advantageous in small electrosurgical instruments which are adapted to fit through trocars having a diameter of five millimeters or less. In such instruments, it is important to have an actuatable blade which is large enough to cut all of the tissue engaged by the jaws of the end effector. In addition, it is important to include a housing which protects the tissue from blade edge 96 when the knife is retracted. It is further necessary to provide sufficient support and stiffness to the wireform-jaw interconnection to ensure that the jaw can firmly grasp and manipulate tissue. The design of tissue stop 18 is particularly adapted to meet those objectives. The elongated shape of blade housing 324 is advantageous because it facilitates the proper positioning of jaws 214 and 216 as end effector 12 is closed, preventing jaws 214 and 216 from being offset as end effector 12 is closed.

Referring now to FIGS. 2 and 3, the operation of a surgical instrument according to the present invention may be described. In FIG. 2, end effector 12 is open, knife button 24 is in its proximal position and trigger 30 is open. When trigger 30 is closed, closure tube 20 slides forward over upper and lower wireforms 14 and 16, closing end effector 12. Alternatively, as illustrated in FIGS. 7–9 in an embodiment of the present invention wherein, for example, jaw 216 is fixed, when trigger 30 is closed, closure tube 20 slides forward over wireform 14, forcing movable jaw 214 against fixed jaw 216 and closing end effector 12. Knife 42 is deployed by moving knife button 24 from its proximal to its distal position in direction B1, thus cutting tissue positioned within end effector 12. Handle latch 44 is adapted to hold trigger 30 in position until released, by, for example, squeezing trigger 30 a second time.

When trigger 30 is moved to its closed position, closure tube 20 is forced to its most distal position. Referring now to FIG. 4 and FIG. 5, as trigger 30 is closed, drive rib 76 moves along cam face 52. Drive rib 76 is forced against cam face 52 by the action of trigger return spring 82 which acts against closure tube washer 80 which engages closure tube 20 and closure tube collar 74. Tissue stop 18, being engaged by the interaction of ribs 88 and 93 with slots 86 and 92 in wireforms 14 and 16 does not move when closure tube 20 moves from its proximal to its distal position. Thus, closure tube 20 slides over tissue stop 18 and wireforms 14 and 16, forcing wireforms 14 and 16 into wireform guide channels 85 and 87. As wireforms 14 and 16 are forced into wireform guide channels 85 and 87, jaws 214 and 216 of end effector 12 are forced together, closing end effector 12. Wireform guide channels 85 and 87 position and align wireforms 14 and 16, thus positioning and aligning jaws 214 and 216 and ensuring that jaw 214 is accurately aligned with jaw 216 as the jaws are closed by the proximal to distal movement of closure tube 20. As trigger 30 is released, trigger return spring 82 forces closure tube collar 74 back by acting on closure tube washer 80. As closure tube 20 moves in a distal to proximal direction, wireforms 14 and 16 move apart, separating wireform jaws 214 and 216 and opening end effector 12. If for some reason closure tube 20 or end effector 12 becomes stuck, the interior face of trigger yoke 50 may be used to force closure tube collar 74 towards the proximal end of the instrument, thus opening the end effector. Handle latch 44 releasably engages trigger latch 36 such that by further pressure on trigger 30, latch 36 is released.

Referring now to FIGS. 4 and 5, knife button 24 is used to move knife blade 94. As knife button 24 is moved in a proximal to distal direction, yoke 62 moves in a proximal to distal direction. Coupler 99 being positioned in hub slot 64, the movement of yoke 62 in a proximal to distal direction moves coupler 99 in a proximal to distal direction. Coupler 99 being attached to push bar 54, movement of coupler 99 in a proximal to distal direction moves push bar 54 axially through closure tube 20 in a proximal to distal direction. Push bar 54 being connected to knife 42, movement of push bar 54 in a proximal to distal direction results in movement of knife 42 in a proximal to distal direction. Thus, movement of knife button 24 in a proximal to distal direction results in movement of knife 42 in a proximal to distal direction. Likewise, movement of knife button 24 in a distal to proximal direction results in movement of coupler 99, push bar 54 and knife 42 in a distal to proximal direction. Push bar 54 moves through closure tube 20 on a line which is substantially parallel to the central axis of closure tube 20. Wireform conductors 14 and 16, which are positioned on either side of push bar 54, pass through coupler 99 such that proximal to distal or distal to proximal movement of coupler 99 does not result in movement of either of wireform conductors 14 or 16.

Referring now to FIGS. 4, 5 and 6, rotation of rotation knob 22 results in rotation of end effector 12, including wireform conductors 14 and 16 and knife 42. When rotation knob 22 is turned or rotated, that rotational motion is transmitted to closure tube washer 80 which rotates closure tube 20. Closure tube 20 being connected to wireform conductors 14 and 16 through closure tube washer 80, rotational movement of closure tube 20 results in rotational movement of wireform conductors 14 and 16. Push bar 54, being positioned between wireform conductors 14 and 16 and attached to knife 42, rotational movement of wireform conductors 14 and 16 results in rotational movement of push bar 54 which, in turn, rotates coupler 99. Coupler 99 rotates freely within hub slot 64 of yoke 62 allowing push bar 54 rotate with wireform conductors 14 and 16.

It will be apparent to those of skill in the art that an instrument including a tissue stop according to the present invention will have a number of advantages. In particular, such a tissue stop will provide a protective cover for the knife blade, preventing it from nicking tissue and reducing the potential for unintentional electrical arcing between the jaws and the blade in an electro-surgical instrument. In addition, as previously stated, the distal face of the tissue stop prevents tissue from getting lodged behind the back of the jaws, facilitating proper cauterization of the tissue. Further, the wireform guide channels in the tissue stop assist in accurately aligning the wireforms and the jaws axially while the ribs in the wireform guide channels assist in accurately aligning the distal end of the jaws. Finally, the tissue stop prevents the retracted knife blade from being pinched by the wireforms when the jaws are closed.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument including a handle, an end effector and an elongated closure tube connected to said handle and adapted to actuate said end effector comprising:
   a tissue stop for use in a surgical instrument, wherein said tissue stop comprises:
      a distal end and a proximal end;
      a body at said proximal end;
      a knife housing at said distal end;
      a neck interconnecting said body and said knife housing;
      a knife blade slot in said knife housing at said distal end;
      a knife channel connecting said distal end to said proximal end through said body, said neck and said housing;
      a first wireform guide channel on a first side of said body; and
      a second wireform guide channel on a second side of said body;
   a first wireform element passing through said elongated tube on a first side of said tissue stop;
   a second wireform element passing through said elongated tube on a second side of said tissue stop;
   a knife positioned within said tissue stop wherein said knife includes a blade positioned in said knife blade slot;
   a knife edge at a distal end of said knife blade such that the entirety of said knife edge is contained within said slot when said knife is in a proximal position.

2. A surgical instrument according to claim 1 wherein said first wireform guide channel includes a rib element adapted to engage a slot in said first wireform element and said second wireform guide channel includes a rib element adapted to engage a slot in said second wireform guide channel.

3. A surgical instrument according to claim 2 wherein said knife includes a knife shank which is moveable within said knife channel, said knife channel providing support for said knife shank.

4. A surgical instrument according to claim 1 wherein said first wireform element is connected to a first jaw of said surgical instrument and said second wireform element is connected to a second jaw of said surgical instrument.

5. An electrosurgical instrument comprising:
   a handle;
   an end effector operatively connected to said handle through an elongated tube;
   first wireform means for supporting a first jaw of said end effector wherein said first wireform means extends from said handle to said first jaw through said elongated tube;
   second wireform means for supporting a second jaw of said end effector wherein said second wireform means extends from said handle to said second jaw through said elongated tube;
   a knife means for cutting tissue, said knife means being moveable within said end effector and including a knife edge at a distal end thereof;
   button means for moving said knife means, said button means being positioned on said handle;
   tissue stop means for positioning tissue engaged by said end effector, wherein said tissue stop means comprises:
      a distal end and a proximal end;
      a body at said proximal end;

a knife housing at said distal end;

a neck interconnecting said body and said knife housing;

a knife blade slot in said knife housing at said distal end; wherein said knife edge is positioned such that the entirety of said knife edge is contained within said knife blade slot when said knife means is in a proximal position;

a knife channel connecting said distal end to said proximal end through said body, said neck and said housing;

a first wireform guide channel on a first side of said body; and a second wireform guide channel on a second side of said body.

6. A surgical instrument according to claim 5 wherein said first wireform guide channel includes a rib element adapted to engage a slot in said first wireform means and said second wireform guide channel includes a rib element adapted to engage a slot in said second wireform means.

7. A surgical instrument according to claim 6 wherein said knife includes a knife shank means adapted to support a knife blade wherein said knife shank is moveable within said knife channel, said knife channel providing support for said knife shank means.

8. A surgical instrument according to claim 5 wherein said first wireform means is connected to a first jaw of said surgical instrument and said second wireform means is connected to a second jaw of said surgical instrument.

9. A surgical instrument according to claim 8 wherein said knife housing is positioned between said jaws and is elongated in a direction parallel to the movement of said jaws.

* * * * *